United States Patent [19]

Justus, deceased

[11] Patent Number: 5,048,353
[45] Date of Patent: Sep. 17, 1991

[54] METHOD AND APPARATUS FOR ROLL PROFILE MEASUREMENT

[75] Inventors: Edgar J. Justus, deceased, late of Beloit, Wis.; by Katherine J. Clayton, executrix, Warren, R.I.

[73] Assignee: Beloit Corporation, Beloit, Wis.

[21] Appl. No.: 486,989

[22] Filed: Mar. 1, 1990

[51] Int. Cl.$^5$ ............................. G01L 1/18; G01L 5/00
[52] U.S. Cl. .................................. 73/862.55; 73/159; 73/862.04
[58] Field of Search .................. 73/865.9, 78, 81, 104, 73/105, 159, 862.04, 862.07, 862.55

[56] References Cited

U.S. PATENT DOCUMENTS

| | | | |
|---|---|---|---|
| 3,194,061 | 7/1965 | Sorenson et al. | 73/81 |
| 3,363,458 | 1/1968 | Scharf et al. | 73/159 |
| 3,425,267 | 2/1969 | Pfeiffer | 73/78 |
| 3,451,258 | 6/1969 | Westbrook | 73/37.7 |
| 3,540,270 | 11/1970 | Wolfer | 73/78 |
| 3,962,911 | 6/1976 | Grenlund | 73/862.67 |
| 4,016,756 | 4/1977 | Kunkle | 73/862.04 |

FOREIGN PATENT DOCUMENTS

| | | | |
|---|---|---|---|
| 15533 | 1/1985 | Japan | 73/862.55 |
| 15534 | 1/1985 | Japan | 73/862.55 |
| 15535 | 1/1985 | Japan | 73/862.55 |
| 183534 | 9/1985 | Japan | 73/862.55 |

Primary Examiner—Tom Noland
Attorney, Agent, or Firm—Dirk J. Veneman; Raymond W. Campbell; Gerald A. Mathews

[57] ABSTRACT

A pressure sensitive device, such as a piezoelectric strip or plurality of piezoelectric crystals, is or are arrayed along the surface of a roll, preferably in a spiral pattern, extending for one revolution of the roll which is nipped with another roll. The nip pressure between the rolls, with or without a paper web passing through the nip, produces a signal by the piezoelectric device indicative of irregularities along the nip. These irregularities, which can be indicative of variations in the web caliper, roll surface, hardness and other parameters of roll or web quality, are then passed to a monitor for continuous read-out of the irregularities or non-uniformities along the face of the roll. Other apparatus, such as a signal conditioner and a signal encoder, can be provided for processing the signals determining the exact axial location along the roll surface of the pressure sensitive device passing through the nip at any given time.

6 Claims, 2 Drawing Sheets

METHOD AND APPARATUS FOR ROLL PROFILE MEASUREMENT

BACKGROUND OF THE INVENTION

1. Field of the Invention

This invention relates to the measurement of irregularities in the cross-machine nip pressure profile of two nipped rolls in the manufacture of web material, such as paper. More specifically, this invention relates to the substantially continuous measurement, in the cross-machine direction, of the irregularities of the nip pressure profile. Still more particularly, this invention relates to the continuous, substantially cross-machine direction, measurement of irregularities, such as hardness, in a wound paper roll by nipping the wound paper roll with a roll having a signal generating strip extending spirally along its surface.

2. Description of the Prior Art

In the winding of an endless web of material, such as paper on the reel of a papermaking machine, slight non-uniformities in sheet thickness, or caliper, become significant when such variations are magnified by the hundreds or thousands of layers of the paper wound on the roll. Such non-uniformities can cause areas of the wound web to burst, or become wrinkled and creased. Further, these variations in uniformity can cause problems in the subsequent converting operations when the continuous paper web is slit and cut into sheets of a size suitable for their eventual use. Even then, if the variations in caliper in the final cut sheets are significant, they can cause problems in the operation of printing machines.

In the manufacture of paper on a papermaking machine, the operator has several tools available to reduce and even eliminate the variations in cross-machine caliper. For example, the calender rolls can be heated or cooled at specific axial locations to increase or decrease the pressure along their nip line of contact. Other adjustments can be made by applying mists of water to the web, changing the slice lip opening at the headbox to modify the basis weight of the web at localized positions, adjusting the dewatering process in the press section, for example, by making crown or deflection adjustments on the rolls in the press section, or heating cross-machine positions of the web by steamboxes.

No matter how the adjustments are made to correct undesirable variations in the paper caliper, such adjustments must be made based on a measurement of the paper web caliper as the web is being formed, pressed, dried or finished on the papermaking machine.

One instrument for measuring web hardness in a wound paper roll is shown and described in Pfeiffer, U.S. Pat. No. 3,425,267. Another apparatus for measuring roll hardness in a roll of paper as it is being wound is shown and described in Wolfer, U.S. Pat. No. 3,540,270.

In the Pfeiffer patent, the instrument is a roll hardness meter which is hand held and is applied by the backtender in a papermaking machine to the paper roll as it is being wound on the reel. The operator must then manually identify the specific location of the non-uniformity along the longitudinal length of the wound paper roll and take corrective action.

In the apparatus shown in the Wolfer patent, a small roller is brought into frictional tracking engagement with the roll of paper as it is being wound and is then guided in a traversing path along the surface of the paper roll parallel to its axis of rotation. The small traversing roller is electrically linked with a signaling device which signals small variations in the surface profile of the roll of paper being wound, which variations are indicative of its hardness. Such hardness is a function of variations in the paper caliper.

The Pfeiffer instrument works well, but it can only be applied to the paper roll by a human operator and only at such locations on the roll and at such times as determined by the operator. Obviously, such times and locations will be randomly and irregularly determined. Just as clearly, any sort of record of such measurements with the Pfeiffer instrument must of necessity be infrequent in the cross-machine direction due to the speed which a human can apply the instrument to a given location on the roll and move to a plurality of successive, uniformly spaced locations longitudinally along the roll. Also, in view of the relative slowness of human movement along the face of the roll of paper being wound, which can exceed 10 meters, and considering the speed of the oncoming paper web, which can exceed 1200 meters/minute for some paper grades, the readings at one end of the roll will not be repeated until literally thousands of meters of paper have been wound onto the paper roll.

In the Wolfer patent apparatus, the roll which traverses the face of the paper roll being wound proceeds uniformly, but its traversing speed is limited and, as a consequence, the cross-machine profile measurements are not made across the width of the paper web in a section of the web approximating a short length of the web in the machine direction. In other words, the measurements do not constitute a cross-machine profile of the web, but, rather, they represent a series of individual measurements which, over a period of time, are taken at successive locations longitudinally along the roll surface.

Since this device must contact the paper roll surface, it may contribute to breaks in the web and in any case, must be retracted whenever the sheet is to be threaded. Further, the cross-machine traversing mechanism can hang up broke.

SUMMARY OF THE INVENTION

The problems associated with the measurement of hardness in a wound roll of paper in the cross-machine direction have been eliminated by this invention. No traversing measuring instrument is required or used in this invention. Instead, in the preferred embodiment of a reel in a papermaking machine, the nip roll, which nips the oncoming paper web against the roll being wound, is equipped with one or a series of uniformly spaced, pressure sensitive elements, such as a piezoelectric crystal, which extend in a spiral pattern along the surface of the nip roll. The spiral pattern is such that it extends circumferentially and uniformly along the surface of the roll for 360 degrees, or less than 360 degrees, in one revolution of the roll. In one embodiment, the pressure sensitive device comprises a piezoelectric film strip which is wrapped uniformly around the surface of the roll along the effective face width of the roll. In another embodiment, a plurality of individual piezoelectric elements are uniformly spaced in a spiral pattern along the surface of the roll.

An angular encoder is linked with the nip roll journal to indicate the angular position of the piezoelectric signal device passing through the nip line of contact with the paper roll being wound relative to a known reference point on the nip roll. Thus, as successive portions of the piezoelectric strip pass through the nip, the angular encoder provides a signal indicative of the circumferential location on the nip roll surface relative to a fixed reference which can be used with an algorithm to locate the cross-machine position of the non-uniformity being reported by the signal being provided by the piezoelectric strip. Since the piezoelectric strip is wound around the nip roll only once, the signals regarding paper roll non-uniformities are provided continuously for the entire cross-machine width of the paper web in increments as narrow as desired and in substantially the cross-machine direction.

These non-uniformities thus produce a cross-machine profile which is useful in determining desired information, such as the hardness of the wound roll and whether the variation in cross-machine web caliper is within desired tolerances.

Accordingly, it is an object of this invention to provide a method and apparatus for determining the cross-machine location of non-uniformities in the nip pressure profile of two cooperating rolls, which may be indicative of corresponding non-uniformities in a traveling web.

It is another object of this invention to provide a method and apparatus for producing signals indicative of non-uniformities in a traveling web of material in the cross-machine direction which does not use a hand held or traversing instrument.

A feature of this invention is the use of one or more pressure sensitive, signal producing means which are associated with the surface of a roll which is brought into nipping engagement with the traveling web of material whose non-uniformities are to be measured, as the traveling web is wound into a roll.

An advantage of the invention is that it provides continuous, uniformly spaced signals of web non-uniformities in the cross-machine direction. This invention, although particularly useful in the measurement of the properties (i.e. hardness) of the wound paper roll, is also useful in any nip, such as a press nip, calender nip, or the like.

These and other objects, features and advantages of the invention will become readily apparent to those skilled in the art upon reading the description of the preferred embodiments in conjunction with the attached figures.

DESCRIPTION OF THE PREFERRED EMBODIMENTS

For purposes of this discussion of the preferred embodiment, the apparatus being referred to is a reel, generally designated with numeral 10, in a papermaking machine. Such reels are well-known in the industry, so the details of the support structure, such as framework, bearings, bearing housings and other common structural components, are not shown in FIG. 1 for purposes of clarity and since they are all thoroughly familiar to the artisan. Accordingly, these common structural components, some of which are shown in FIG. 1A, will not be further described.

Figure 1:
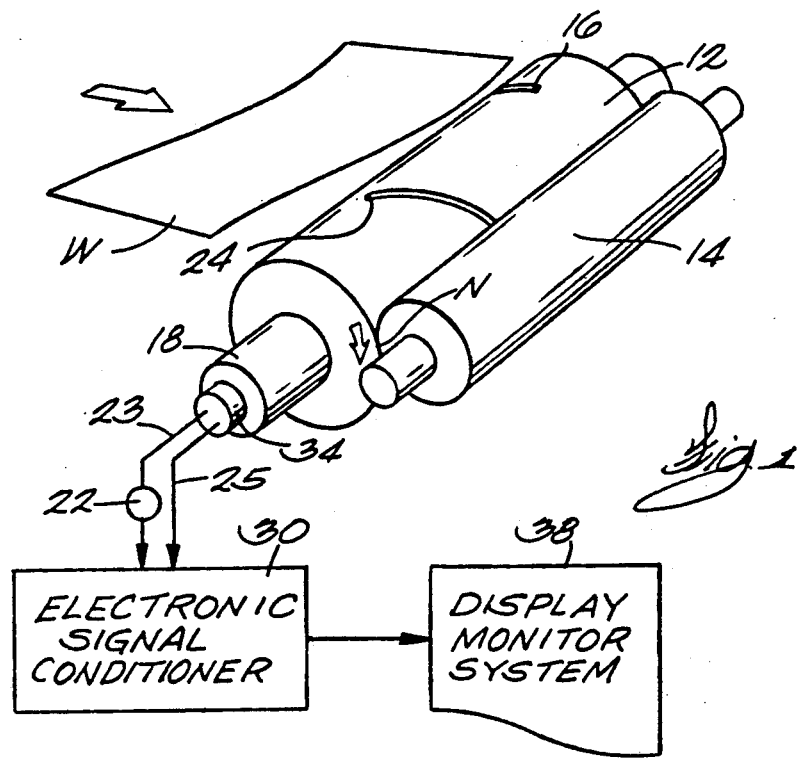
FIG. 1 is a perspective view of a papermaking machine reel showing, in somewhat schematic form, the nip roll in engagement with the paper roll being wound.
Figure 1A:
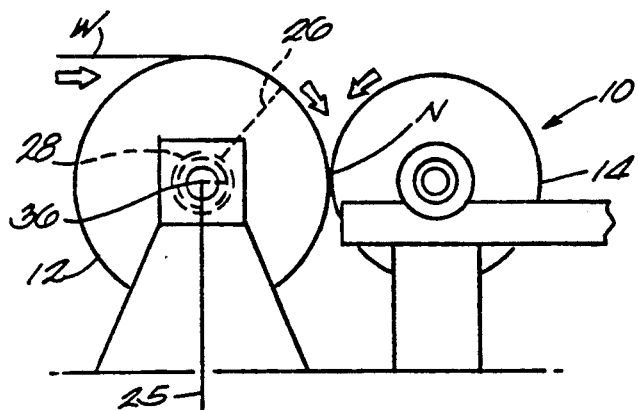
FIG. 1A is an end-elevational view of the type of apparatus shown in FIG. 1, but showing more of the reel framework and showing the web passing over the nip roll and into its nip with the paper roll as it is wound up.

With reference to FIGS. 1 and 1A, a nip roll 12, which is the reel drum in a papermaking machine reel, is shown in nipping engagement along a nip line of contact N with a paper roll 14 on which is being wound the traveling paper web W. A piezoelectric film strip 16 is shown mounted on the surface of the nip roll 12 in a helix, or spiral, extending for the face width of the roll.

In this discussion, the effective face width FW is that longitudinal length of the nip roll surface equal to the width of the paper web W being wound on the paper roll. The effective face width FW in web processing machinery, such as on a papermaking machine, is normally somewhat shorter than the total length L of the nip roll surface, but there is no reason why the effective face width FW could not equal the length L of the nip roll. These lengths, and their relationship with the piezoelectric strip, are shown more clearly in FIG. 3.

At the end of journal 18 of the nip roll 12 is mounted an angular encoder 22, via line 23, to provide a signal based on the radial displacement of a point on the nip from a fixed point on the roll, such as the end 24 of the piezoelectric film strip 16. The piezoelectric film strip, in turn, has an electrical lead 26 extending from the strip 16 to the journal of the roll, then through some suitable connection, such as slip rings 28, shown with dashed lines in FIG. 1A, which lead, via line 25, to an electronic signal conditioner 30.

Figure 2:
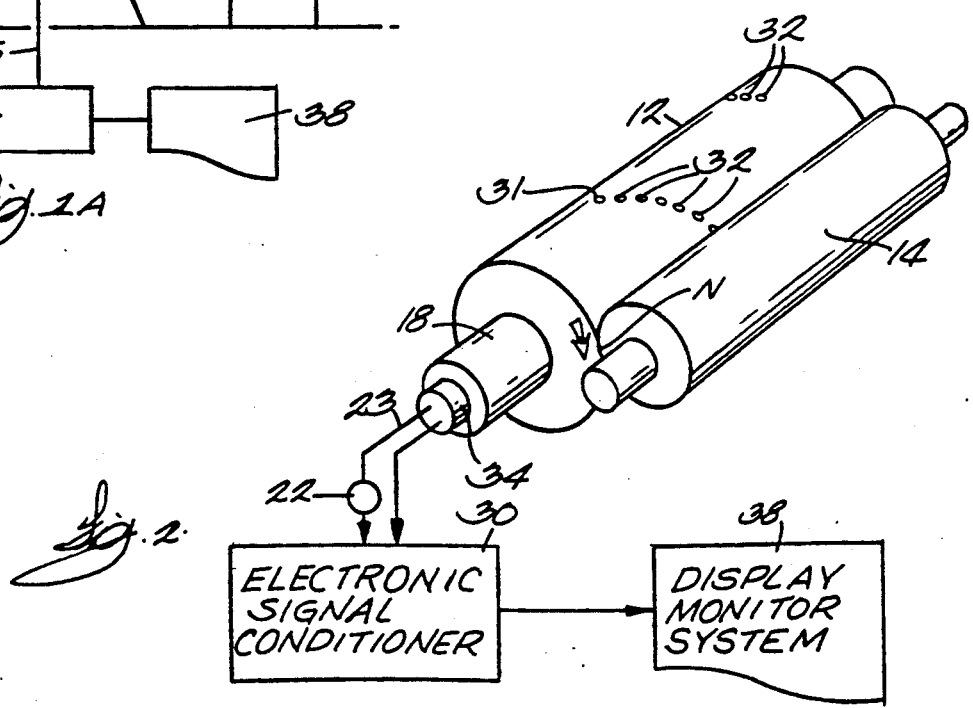
FIG. 2 is a perspective view substantially similar to the view shown in FIG. 1, but wherein the signal producing elements comprise a series of piezoelectric crystals disposed in a spiral pattern in the nip roll.
Figure 2A:
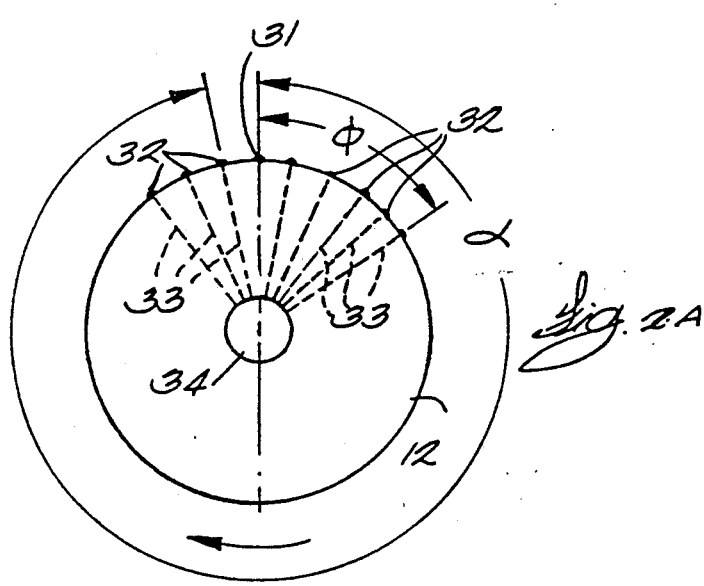
FIG. 2A is an end-elevational schematic view of a nip roll of the type shown in FIG. 2 showing the angular location of individual piezoelectric crystals extending almost all about the circumference of the roll.

The apparatus shown in FIGS. 2, 2A is similar to that shown in FIG. 1. However, in FIG. 2, the single, elongate piezoelectric film strip 16 is replaced by a plurality of individual piezoelectric crystals 32 which extend in the same type of spiral path along the surface of the nip roll 12 as did the film strip 16. Each of the individual crystals 32 is linked, via electrical lead lines 33, with a multiplexer 34, in the manner shown schematically in FIGS. 2, 2A. The end piezoelectric crystal corresponding to end 24 of strip 16 is designated as crystal 31.

In both the embodiments shown in FIGS. 1 and 2, the piezoelectric film strip 16, or the plurality of individual piezoelectric crystals 32, preferably extend for one complete trip around the circumference of the nip roll such that a reading from the piezoelectric device or devices is given for each desired angular position of the nip roll 12 during its rotation. Alternately, the plurality of individual piezoelectric crystals 32 extend in a straight axial direction across the face of the roll. In this alternative embodiment, the individual crystals may be monitored simultaneously or sequentially as they pass through the nip.

Figure 3:
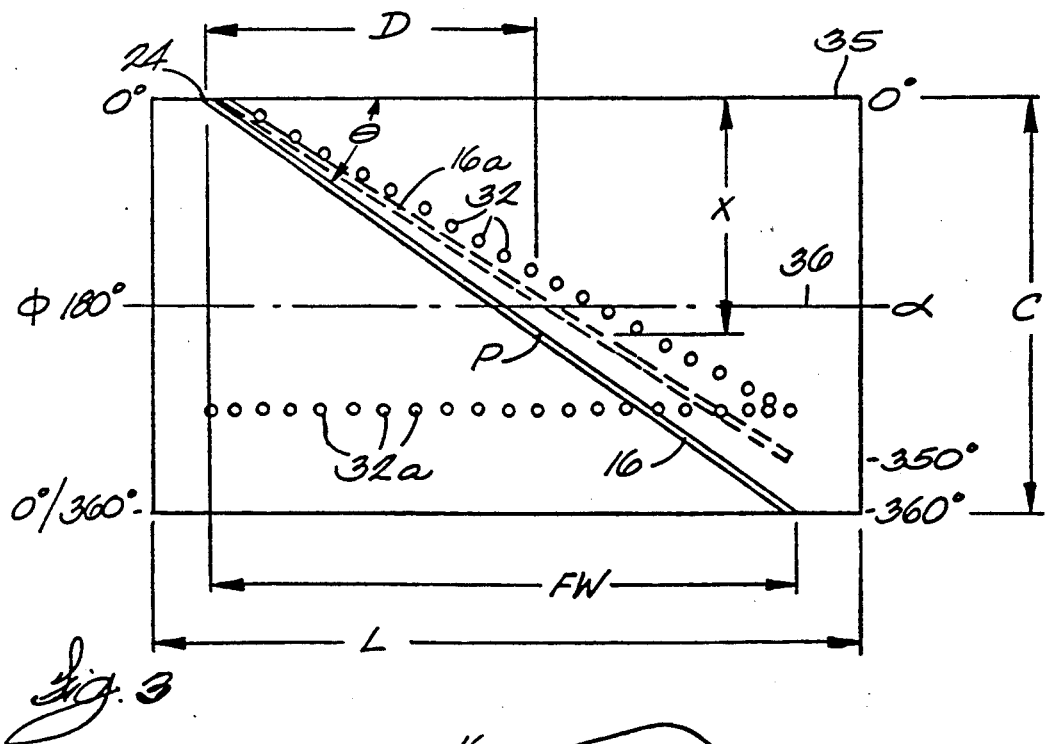
FIG. 3 is a plan view of a nip roll cover, or surface, showing four different configurations of the signal producing elements along the surface of the nip roll.

FIG. 3, which is a plan view of the surface of nip roll 12, illustrates how the location of a point of irregularity in the web being wound into the paper roll 14 might be located along the nip N. The location of a given point P along the piezoelectric film strip 16 can be determined knowing the angle $\theta$ of the film strip relative to a line 35 extending longitudinally along the surface parallel with the axis of rotation 36 of nip roll (reel drum) 12. In other words, $\theta$ is the angle of the helix of film strip 16 on the surface of the reel drum if it was cut along longitudinal line 35 and is spread flat as shown in FIG. 3.

The reference point on the roll 12 is selected at 0°, such as at points 24,31 and $\phi$ is measured angularly about the axis of rotation 36 from there in radians. This 0° reference point is also where the end 24 of the film strip 16 and end crystal 31 of the helically extending string of crystals 32 are located. The distance D is the longitudinally extending coordinate of point P on the surface of roll 12 parallel with the axis of rotation 36 of roll 12 at a given angular location $\phi$. Point P can be either a specific location on strip 16 or a specific crystal 32. X is the circumferentially extending coordinate of point P.

The distance X is determined by multiplying the radius r of nip roll 12 times the angle $\phi$ in radians. Thus, X equals $r\phi$. The circumference of the roll 12 is shown as C. Then the ratio X/C equals $r\phi/2\pi r$ or X equals C $(\phi/2\pi)$.

Still referring to FIG. 3, $\tan \theta$ equals X/D or D equals X/$\tan \theta$. Substituting X equals $C\theta/2\pi$, D equals $C\theta/2\pi \tan \theta$. Since the circumference C equals $2\pi r$, D equals $2\pi r \phi/2\pi \tan \theta$, or D equals $r\phi/\tan \theta$. This value of D tells the signal conditioner, which signals the display monitor 38 via line 39, where the reading is being made longitudinally along the roll face.

Figure 4:
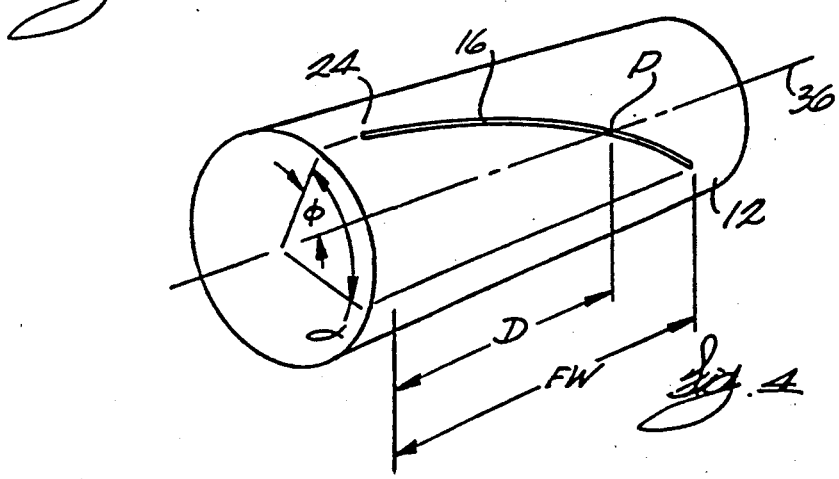
FIG. 4 is a perspective view of a piezoelectric strip disposed on a roll and extending circumferentially for an angle $\alpha$ along the face width.

With reference to FIG. 4, another algorithm for determining the axial location of a selected point along a helically extending piezoelectric strip, or string of crystals, in a nip between two rolls is to relate the angular location $\phi$ of the selected point P circumferentially from a fixed reference, such as the beginning of the strip 24, or initial piezoelectric crystal 31, to the total circumferential wrap $\alpha$ of the strip, which is a predetermined, fixed value, or string of crystals in its, or their, helical path about the roll surface. Thus, for example, the total circumferential wrap $\alpha$ of the strip is 90° and the distance D is desired at an angular position of 45°, then D simply equals FW$\phi/\alpha$ or D equals FW/2. The computation of D, using this algorithm, does not involve the use of the roll radius or helix angle $\theta$, such as used in FIG. 3, but the depiction of D in FIG. 4 is more difficult to illustrate.

In operation, with reference to FIGS. 1 and 1A, reel drum 12 brings the web W into nipping engagement with paper roll 14 to wind the web thereon. The continuous piezoelectric film strip 16, which extends spirally about the surface of nip roll 12 for one complete revolution, always has one part of it passing through the nip line of contact between rolls 12,14. Since the piezoelectric film strip operates on the principle that the electric signal produced is a function of the pressure exerted on it, the corresponding high and low spots in the profile of the paper web are indicated by the signal of the piezoelectric film strip as it passes through the nip producing a continuous signal corresponding to the particular irregularity at the point P passing through nip N. This signal is passed out through slip rings 28 via electrical lead line 25 to an electronic signal conditioner 30 which correlates the piezoelectric signal with the signal provided by the angular encoder 22 to produce a continuous display in the display monitoring system 38 of the irregularity in the web at a particular location axially along the roll based on an algorithm such as, for example, the one described above which is provided to the signal conditioner.

With reference to FIG. 3, piezoelectric film strip 16 extends completely around the reel drum roll 12 which is indicated as extending from 0°–360°. This produces a continuous display wherein only the reading for the portion of the film strip passing through the nip N changes with the other readings on the display monitor remaining the same until the portion of the film strip corresponding to a particular reading passes through the nip, is re-read and changed.

An alternative arrangement is shown in FIG. 3 wherein film strip 16a is arrayed to extend for the effective face width FW, but does not completely wrap the roll circumference. Instead, the film strip stops at some circumferential wrap $\alpha$ location short of 360° such as, for example, 350° as shown. This produces an interruption in the signal each revolution of roll 12. The signal conditioner 30 can utilize this interruption to reset the display on the display monitoring system 38 to zero. The readings then always start from a particular location and appear sequentially on the monitoring system read-out or screen. This might be preferred in some situations because the angular encoder would not then be required since the initial points 24,31 passing through the nip would produce or spike in the signal conditioner which would enable it to determine the axial location of the strip or crystals passing through the nip based on when points 24,31 passed through.

Also shown in FIG. 3, for purposes of illustration, is a plurality of individual piezoelectric crystals 32 which are arrayed in a helical pattern like strip 16 and a plurality of crystals 32a which are arrayed longitudinally along the surface of the roll parallel to the axis of rotation 36.

The apparatus shown in FIGS. 2, 2A, operates on the same principle except that each individual piezoelectric crystal 32 is separately connected to the electronic signal conditioner 30 via a multiplexer 34 to which individual electrical leads 40 from each crystal 32 are connected. The location of the particular piezoelectric crystal is known, or computed, by the angular encoder 22 which is connected to the multiplexer, and the irregularity based on the piezoelectric signal is displayed in the display monitoring system 38. The multiplexer can be interrogated by the signal conditioner to read the signals from one or more crystals 32 as desired.

Thus, regardless of the form of the piezoelectric apparatus, a cross-machine signal is generated for each revolution of nip roll 12 for each selected location along the face of the paper roll 14 for the longitudinal distance of the effective face width FW. The invention is simple and provides a cross-machine profile reading of the irregularities or non-uniformities in the web, which can be a function of the hardness of the wound roll of paper on a papermaking machine reel, for each location along the width of the paper web in no longer than the distance of web travel equal to the circumference of the nip roll 12.

Naturally, variations in the invention can be made without departing from the spirit and scope of the appended claims which alone limit the scope of the invention. In this regard, it is anticipated that the concepts of the invention can be utilized in various types of apparatus, such as winders and calenders, in addition to reels.

Also, a double helix array of piezoelectric film strips 16 could be used to provide additional readings at shorter intervals, as desired.

What is claimed is:

1. Apparatus for producing a reading indicative of non-uniformities in the cross-machine nip pressure profile of two cooperating rolls, comprising, in combination:

first and second rolls with a nip line of contact therebetween;

pressure sensitive means arrayed in the cross-machine direction on the surface of the first roll along a face width thereof and arranged in a uniform spiral for less than 360°, said pressure sensitive means being capable of producing a first signal corresponding to the nip force applied by the mating roll against the pressure sensitive means;

signal conditioning means for receiving the first signal and producing a read-out signal indicative of the nip force at predetermined locations across the surface of the roll as determined by the pressure sensitive means passing through the nip;

display monitoring means for receiving the read-out signal and providing a display of the read-out signals at lateral points across the surface of the roll indicative of the nip pressure profile along the nip line;

the interruption in the first signal produced by a gap in the pressure sensitive means not passing through the nip is utilized by the signal conditioning means to reset the third signals passed to the display monitoring means.

2. Apparatus for producing a reading indicative of non-uniformities in the cross-machine nip pressure profile of two cooperating rolls, comprising, in combination:

first and second rolls with a nip line of contact therebetween;

a continuous piezoelectric strip arrayed in a continuous uniform spiral about the surface of the first roll for 360°, said piezoelectric strip being capable of producing a first signal corresponding to the nip force applied by the mating roll against the piezoelectric strip;

signal conditioning means for receiving the first signal and producing a read-out signal indicative of the nip force at predetermined locations across the surface of the roll as determined by the piezoelectric strip passing through the nip;

display monitoring means for receiving the read-out signal and providing a display of the read-out signals at lateral points across the surface of the roll indicative of the nip pressure profile along the nip line.

3. Apparatus for producing a reading indicative of non-uniformities in the cross-machine nip pressure profile of two cooperating rolls, comprising, in combination:

first and second rolls with a nip line of contact therebetween;

a plurality of individual piezoelectric crystals arrayed uniformly in a spiral in the cross-machine direction on the surface of the first roll, said piezoelectric crystals each being capable of producing a first signal corresponding to the nip force applied by the mating roll;

signal conditioning means for receiving the first signal and producing a read-out signal indicative of the nip force at predetermined locations across the surface of the roll as determined by the piezoelectric crystals passing through the nip;

a multiplexer for receiving the signals from the individual piezoelectric crystals, said multiplexer being electrically linked with the signal conditioning means to pass successive signals from piezoelectric crystals passing through the nip to the signal conditioning means;

display monitoring means for receiving the read-out signal and providing a display of the read-out signals at lateral points across the surface of the roll indicative of the nip pressure profile along the nip line.

4. Apparatus for producing a reading indicative of non-uniformities in the cross-machine nip pressure profile of two cooperating rolls, comprising, in combination:

first and second rolls with a nip line of contact therebetween;

pressure sensitive means arrayed in the cross-machine direction on the surface of the first roll and extending spirally around the roll surface along a face width thereof for 360°, said pressure sensitive means being capable of producing a first signal corresponding to the nip force applied by the mating roll against the pressure sensitive means;

signal conditioning means for receiving the first signal and producing a read-out signal indicative of the nip force at predetermined locations across the surface of the roll as determined by the pressure sensitive means passing through the tip;

encoder means for providing a second signal indicating the angular position of the nip force on the pressure sensitive means relative to a fixed reference on the first roll, said second signal being produced at predetermined time intervals;

said signal conditioning means receiving the second signal and correlating it with the first signal to produce the read-out signal;

display monitoring means for receiving the read-out signal and providing a display of the read-out signals at lateral points across the surface of the roll indicative of the nip pressure profile along the nip line.

5. Apparatus for producing a reading indicative of non-uniformities in the cross-machine nip pressure profile of two cooperating rolls for processing a traveling web comprising, in combination:

first and second rolls for engaging the traveling web along a nip line of contact therebetween;

pressure sensitive means spirally arrayed on the surface of the first roll along a face width thereof, said pressure sensitive means being capable of producing a first signal corresponding to the nip force applied in the contact between the web and the pressure sensitive means;

encoder means for providing a second signal indicating the angular position of the nip force on the pressure sensitive means relative to a fixed reference on the first roll, said second signal being produced at predetermined time intervals;

signal conditioning means for receiving the first signal and correlating it with a second signal and producing a read-out signal indicative of the nip force across the surface of the web;

display monitoring means for receiving the read-out signal and providing a display of the read-out signals at lateral points across the surface of the web indicative of the web profile along the nip line.

6. A method for producing a reading indicative of non-uniformities in the cross-machine profile of a traveling web of material comprising, in combination:

nipping the traveling web between first and second rolls along a nip line of contact therebetween;

providing pressure sensitive means spirally arranged on the surface of the first roll along a face width thereof to produce a first signal indicative of the force of the nip on the web against the pressure sensitive means as the pressure sensitive means passes through the nip;

determined the angular location of the position of the pressure sensitive means in the nip relative to a fixed reference on the first roll;

correlating the first signal with the angular position and producing a read-out signal indicative of the nip force against the pressure sensitive means and its lateral location in the cross-machine direction across the web;

displaying a predetermined number of readings of the read-out signal indicative of the web profile in the cross-machine direction.

* * * * *